_United States Patent_ [19]

Alfano et al.

[11] Patent Number: 5,315,437
[45] Date of Patent: May 24, 1994

[54] PROTECTIVE DEVICE FOR SELECTIVELY REFLECTING HIGH-INTENSITY LIGHT OVER A BROAD SPECTRAL BANDWIDTH

[76] Inventors: Robert R. Alfano, 3777 Independence Ave., Bronx, N.Y. 10463; Kwong M. Yoo, 412 W. 148th St., Apt. 2G, New York, N.Y. 10031

[21] Appl. No.: 884,038

[22] Filed: May 21, 1992

Related U.S. Application Data

[63] Continuation-in-part of Ser. No. 685,964, Apr. 12, 1991, which is a continuation of Ser. No. 322,439, Mar. 13, 1989, abandoned.

[51] Int. Cl.$^5$ .............................................. G02B 5/28
[52] U.S. Cl. .................................. 359/588; 359/326; 359/586; 359/589
[58] Field of Search ............................. 359/326–332, 359/580, 584, 586, 588, 589, 615, 652–654

[56] References Cited

U.S. PATENT DOCUMENTS

| | | | |
|---|---|---|---|
| 4,884,868 | 12/1989 | Böhm | 359/615 |
| 4,926,366 | 5/1990 | Cuykendall et al. | 364/713 |
| 5,200,858 | 4/1993 | Hagerty et al. | 359/652 |

OTHER PUBLICATIONS

Yoo et al., "Nonlinear Photon Localization For...", _Optics Letters_, vol. 16, No. 23, Dec. 1991, pp. 1823–1825.

_Primary Examiner_—John D. Lee
_Attorney, Agent, or Firm_—Kriegsman & Kriegsman

[57] ABSTRACT

A protective device designed to protect eyes and sensitive photodetectors from high-intensity light over a broad spectral bandwidth while permitting low-intensity and ambient light to be transmitted thereto. In a first embodiment, the device comprises a stack of nonlinear materials having the same linear index of refraction but alternating between a relatively high nonlinear index of refraction and a relatively low nonlinear index of refraction. The respective optical thicknesses of the nonlinear materials are unordered. In a second embodiment, the device comprises a stack of nonlinear materials having the same linear index of refraction and the same optical thickness of a one-half wavelength but unordered nonlinear indices of refraction. In a third embodiment, the device comprises a stack of nonlinear materials having linear indices of refraction alternating between a relatively high linear index of refraction and a relatively low index of refraction and nonlinear indices of refraction which are unordered. The respective optical thicknesses of the nonlinear materials are designed so that the materials are optimally transmissive in the linear domain. In a fourth embodiment, the device comprises a stack of nonlinear materials having the same linear index of refraction but unordered optical thicknesses and nonlinear indices of refraction.

17 Claims, 9 Drawing Sheets

PROTECTIVE DEVICE FOR SELECTIVELY REFLECTING HIGH-INTENSITY LIGHT OVER A BROAD SPECTRAL BANDWIDTH

The U.S. Government has a paid-up license in this invention and the right in limited circumstances to require the patent owner to license others on reasonable terms as provided for by the terms of Grant No. 447288 awarded by the Air Force Office of Scientific Research

BACKGROUND OF THE INVENTION

The present application is a continuation-in-part of presently pending U.S. Ser. No. 07/685,964, filed Apr. 12, 1991 which is a continuation of abandoned U.S. Ser. No. 07/322,439, filed Mar. 13, 1989.

The present invention relates generally to multilayer coatings designed to function as high-reflectance mirrors.

High-intensity light of the type emitted, for example, from a laser or the like can cause severe damage to the human eye as well as to sensitive photodetectors. Unfortunately, many devices which are designed to protect a person's eyes or a sensitive photodetector from high-intensity light are limited in that they reflect light based solely on its wavelength, regardless of the intensity of the light. In addition, such devices are also limited in that they are typically specific for light only within a relatively narrow bandwidth. Other protective devices which are designed to reflect light of a broader spectral bandwidth are typically darkly colored and allow little ambient light to be transmitted therethrough for vision.

As can readily be appreciated, there is a great need for a protective device which is capable of preventing high-intensity light from being transmitted to an eye or to a sensitive photodetector and, yet, is still capable of transmitting ambient and low-intensity light thereto.

SUMMARY OF THE INVENTION

Accordingly, it is an object of the present invention to provide a protective device which is capable of reflecting high-intensity light while transmitting ambient and low-intensity light.

It is another object of the present invention to provide a protective device as described above which is capable of functioning over a broad spectral bandwidth.

It is still another object of the present invention to provide a protective device as described above which is capable of switching rapidly between a highly transmissive state and a highly reflective state in response to the incidence of high-intensity light thereonto.

In accordance with the purpose of the present invention as broadly set forth above, there is provided a first embodiment of a protective device designed to selectively reflect an incident beam of high-intensity light over a broad spectral bandwidth, the protective device comprising a stack of non-linear materials, each of the non-linear materials in said stack possessing a linear index of refraction, a non-linear index of refraction, and an optical thickness, the respective linear indices of refraction of the non-linear materials being the same, the respective non-linear indices of refraction of the non-linear materials alternating between a high non-linear index of refraction and a low non-linear index of refraction, and the respective optical thicknesses of the non-linear materials being unordered, whereby when a beam of high-intensity light over a broad spectral bandwidth is caused to propagate through said stack, a random phase shift is introduced into the beam at the interface of adjacent non-linear materials, cumulatively resulting in a high degree of reflectance of said beam.

Also in accordance with the purpose of the present invention as broadly set forth above, there is provided a second embodiment of a protective device designed to selectively reflect high-intensity light over a broad spectral bandwidth, the protective device comprising a stack of non-linear materials, each of the non-linear materials in said stack possessing a linear index of refraction and a non-linear index of refraction, the respective linear indices of refraction of the non-linear materials being the same, the respective non-linear indices of refraction of the non-linear materials being unordered, whereby when a beam of high-intensity light over a broad spectral bandwidth is caused to propagate through said stack, a random phase shift is introduced into the beam at the interface of adjacent non-linear materials, cumulatively resulting in a high degree of reflectance of said beam.

Further in accordance with the purpose of the present invention as broadly set forth above, there is provided a third embodiment of a protective device designed to selectively reflect high-intensity light over a broad spectral bandwidth, the protective device comprising a stack of non-linear materials, each of the non-linear materials in said stack possessing a linear index of refraction, a non-linear index of refraction, and an optical thickness, the respective linear indices of refraction of the non-linear materials alternating between a high index of refraction and a low index of refraction, the respective optical thicknesses of the non-linear materials being selected so that said stack of non-linear materials functions in the linear domain as an anti-reflection coating, the respective non-linear indices of refraction of the non-linear materials being unordered, whereby when a beam of high-intensity light over a broad spectral bandwidth is caused to propagate through said stack, a random phase shift is introduced into the beam at the interface of adjacent non-linear materials, cumulatively resulting in a high degree of reflectance of said beam.

For purposes of the present specification and claims, the term "unordered," when used to describe one or more characteristics of a stack of non-linear materials, such as the respective non-linear indices of refraction of the stack of non-linear materials and/or the respective optical thicknesses of the stack of non-linear materials, is intended to convey the complete absence of any pattern or nexus over a substantial portion of the stack of non-linear materials between the characteristic in question and one or more desired qualities of the stack. A pattern or a nexus may be evidenced, for example, by an arithmetic, geometric or other formulaic progression of the characteristic in the stack based on one or more desired qualities of the stack or by constancy in the given characteristic in the stack based on one or more desired qualities of the stack. The absence of a pattern or nexus for a given characteristic is not established merely by the inexactness of a manufacturing technique, unless said manufacturing technique results in the value of the characteristic in question being totally unrelated to what was intended. An "unordered" arrangement of the type envisioned by the present invention may be produced, for example, by a computer having a random number generator. To guard against the unlikely possibility that the random number generator will randomly select a series of values that happen to correspond to a pattern over a substantial portion of the stack, one may use software to post-screen the randomly selected numbers.

Additional objects, features, and advantages of the present invention will be set forth in part in the description which follows, and in part will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In these drawings wherein like reference numerals represent like parts.

DETAILED DESCRIPTION OF PREFERRED EMBODIMENTS

As discussed above, the present invention is directed to a protective device for selectively reflecting high-intensity light over a broad spectral bandwidth. The protective device of the present invention comprises a multilayer coating of non-linear materials, the layers being designed for a high degree of transmission of light in the linear domain, i.e., for low-intensity and ambient light, and for a high degree of reflectance of light in the non-linear domain, i.e., for high-intensity light. In accordance with the teachings of the present invention, high-reflectance in the non-linear domain is achieved by arranging the various layers in the coating so that their respective optical thicknesses and/or their respective non-linear indices of refraction are unordered. Consequently, light propagating through the multilayer coating is subjected to a random phase shift as it transits through the interface of adjacent layers, cumulatively resulting in a high degree of reflectance of the light.

Figure 1:
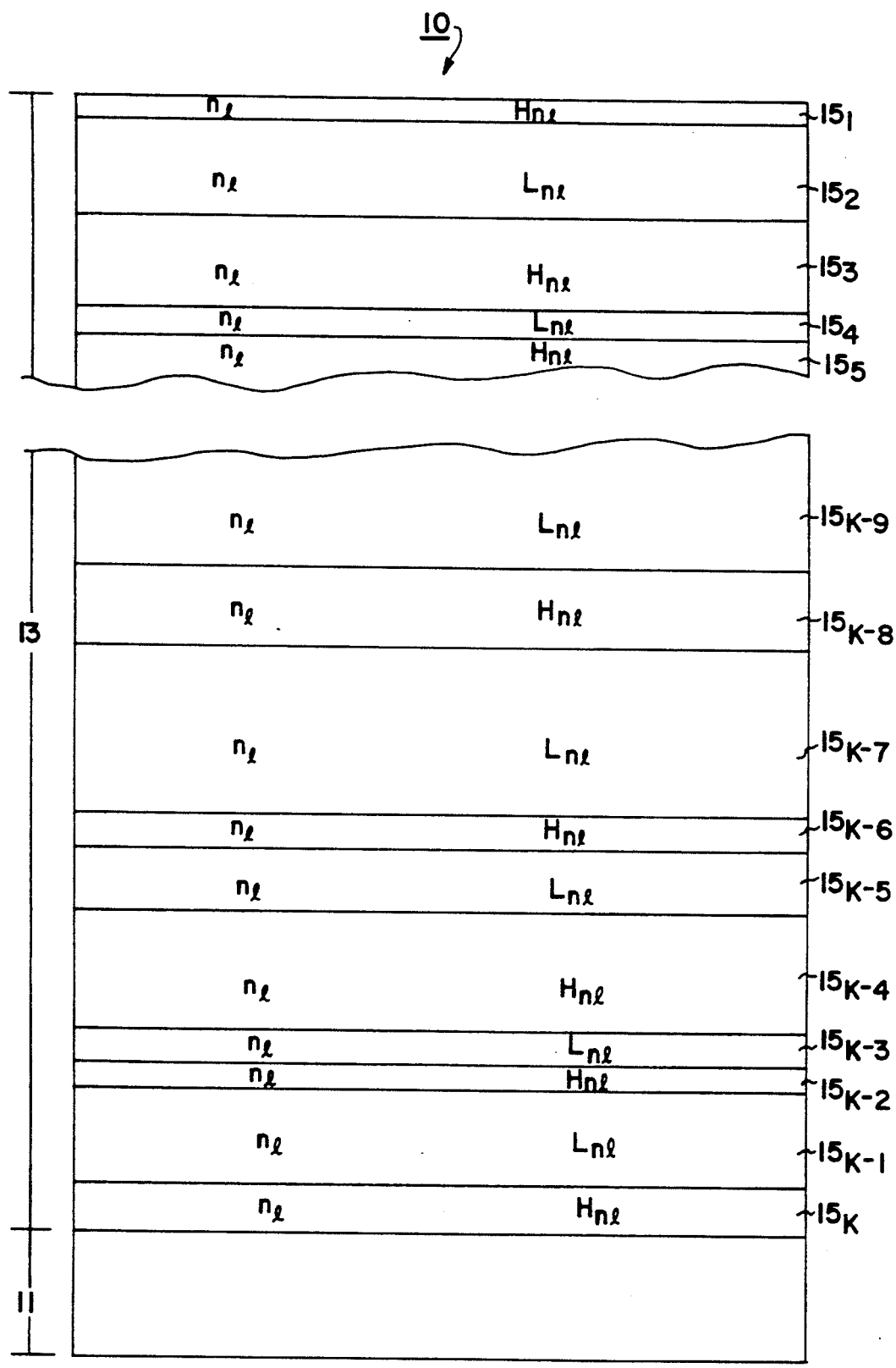
FIG. 1 is a schematic representation of one embodiment of a protective device designed to selectively reflect an incident beam of high-intensity light over a broad spectral bandwith, the protective device being constructed according to the teachings of the present invention.

Referring now to FIG. 1, there is shown one embodiment of a protective device designed to selectively reflect an incident beam of high-intensity light over a broad spectral bandwidth, the protective device being constructed according to the teachings of the present invention and being represented by reference numeral 10.

Device 10 includes a transparent substrate 11 and a multilayer coating 13, coating 13 being affixed to substrate 11. Where, for example, device 10 is to be used as protective eyewear for a person, substrate 11 may be made of the same material typically used in eyeglass lenses, such as glass, plastic or the like.

Coating 13 comprises a stack of non-linear materials $15_1$ through $15_k$, respectively. All of the non-linear materials in the stack possess substantially the same linear index of refraction ($n_l$). As can readily be appreciated, this constancy in the linear index of refraction permits low-intensity and ambient light to pass through the stack substantially unaffected. In addition, each of the non-linear materials in the stack also possesses either a relatively high non-linear index of refraction ($H_{nl}$) or a relatively low non-linear index of refraction ($L_{nl}$), the high non-linear index materials alternating with the low non-linear index materials. It should be recognized that the respective high non-linear index materials may be either the same material or different materials and may possess either the same index of refraction or different indices of refraction. Similarly, it should be recognized that the respective low non-linear index materials may be either the same material or different materials and may possess either the same index of refraction or different indices of refraction.

As will be seen below, the percentage of high-intensity light reflected by coating 13 is expected to increase as the difference between the high non-linear indices of refraction and the low non-linear indices of refraction increases.

Each of non-linear materials $15_1$ through $15_k$ also has an optical thickness. In accordance with the teachings of the present invention, the respective optical thicknesses of the materials are unordered, typically varying in an undefined manner between an upper limit and a lower limit. Selection of the values corresponding to the optical thicknesses of the respective non-linear materials can be achieved, for example, by means of a random number generator of the type typically found in a computer (either by having the random number generator directly select random values corresponding to the respective optical thicknesses of the layers or by having the random number generator randomize the order of a more limited class of possible optical thicknesses). To avoid the astronomically-remote possibility that the random number generator may select values which happen to be identical to those values which would be present in an ordered system, one may wish to use some sort of post-selection screening of numbers. This can easily be performed, for example, through software implemented by the same computer possessing the random number generator.

As will become apparent from the discussion below, as the difference between the upper limit and the lower limit of the range of optical thicknesses increases, the spectral bandwidth of high-intensity light for which device 10 is operative typically will broaden.

The invention may best be understood by the following detailed explanation of the underlying theory.

Photon localization, which is described, for example, in Yoo et al., Phys. Rev. B, Vol. 39, pp. 5806–5809 (1989), which is incorporated herein by reference, and non-linear optics are the underlying physical principles for the present invention. Photon localization of the random one-dimensional system gives rise to the characteristic of broad bandwidth of high reflection. In a one-dimensional system, such as a multilayer dielectric system, light cannot pass through but will be totally reflected over a broad spectrum if the phase shift for each layer fluctuates in an unordered way. Total reflection will occur even with infinitesimally small amounts of randomness in phase shift if the number of layers is sufficiently large. The transmission of the low-intensity light is determined by the linear refractive indices of the multilayer system, which can be designed to transmit the ambient light totally. In order to reduce the transmission of the multilayer system as the radiation intensity increases, the system is made of alternating high and low nonlinear materials, and the thickness of each layer is unordered. The refractive indices of each layer can then be changed and regulated by the radiation intensity by means of the induced nonlinear refractive index. These induced refractive indices change the interface reflectance and randomize the phase shift of each layer, creating a random one-dimensional system. This induced random one-dimensional system regulates the reflection of the radiation and actively depends on the radiation intensity. The higher the radiation intensity, the higher is the change in the refractive indices, which results in higher reflection for the high-intensity light.

The reflectance of a multilayer system can be computed numerically by Rouard's method and is determined by the reflectance at the interface k, $r_k$, and the phase shift at layer k, $\delta_k$, which are given by:

$$r_k = (n_k \cos \theta_k - n_{k+1} \cos \theta_{k+1})/(n_k \cos \theta_k + n_{k+1} \cos \theta_{k+1}) \quad (1)$$

$$\delta_k = 2\pi n_k d_k/(\lambda \cos \theta_k) \quad (2)$$

where $n_k$ is the refractive index, $\theta_k$ is the angle of incidence, $d_k$ is the thickness of the layer, subscript k refers to layer k, and $\lambda$ is the wavelength of the light.

The refractive index of the kth layer is written as $$n_k = n_{lk} + n_{nlk}, \quad (3)$$

where $n_{lk}$ and $n_{nlk}$ are the linear and nonlinear refractive-index components, respectively. The nonlinear index is proportional to the light intensity, $$n_{nl} = n_2 E^2, \quad (4)$$

where $n_2$ is the nonlinear index coefficient. The value of $n_2$ for materials varies from $10^{-4}$ to $10^{31\ 12}$ esu depending on the response time of the material. The refractive index of the material for low-intensity light is equal to $n_l$ since $n_{nl}$ is negligibly small. The ambient light transmission in the multilayer system is determined by the linear component of the refractive index. A well-known example of a multilayer system that transmits the ambient light is an anti-reflection coating.

The transmission characteristics of the multilayer system change as the refractive indices are changed by the radiation intensity through induced nonlinear indices. The performance of the multilayer system for rejecting the high-intensity laser are illustrated by the following examples, which will lay down the criteria for fabricating the novel protective optical radiation devices. The reflection of the multilayer system is computed numerically. The multilayer system illustrated here consists of alternating high and low nonlinear materials, where the nonlinearity of the high-index material is much higher than that of the low-index material. The change in refractive index of the low-index material induced by high-intensity radiation is assumed to be negligible as compared with that of the high-index material. The thickness of each layer is unordered. These two materials are chosen to have the same linear refractive index in order to transmit the ambient light totally because $r_k = 0$. A high-intensity laser radiation induces a change in the refractive index through $n_2$ such that $r_k$ is no longer equal to zero. With a combination of nonzero $r_k$ and the random phase shift of each layer, the system can be designed to reflect high-intensity light.

Figure 2A:
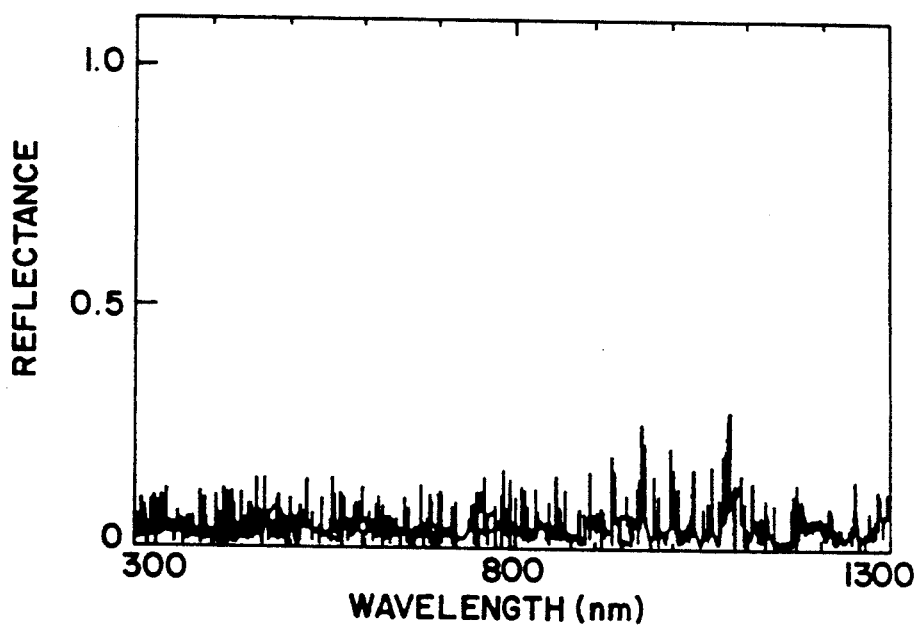
FIGS. 2(a) through 2(d) are computer-generated graphic representations of the reflectance of light as a function of wavelength for a device of the type shown in FIG. 1 wherein the number of layers is 400, wherein the linear index of refraction ($n_l$) for each layer is 1.5, wherein the non-linear index of refraction ($n_{nl}$) for the high index materials as a result of being induced by a high-intensity beam of light is 0.01 $n_l$, 0.08 $n_l$, 0.2 $n_l$, and 0.8 $n_l$, respectively, and wherein the optical thickness of each layer is unordered, fluctuating between 180 nm and 580 nm with a mean thickness of about 380 nm.
Figure 2B:
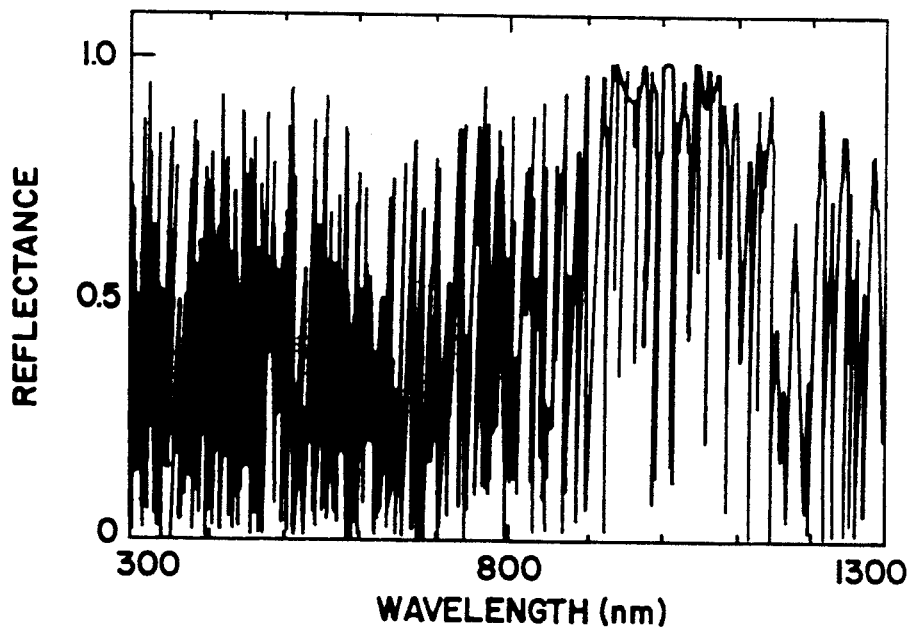
Figure 2C:
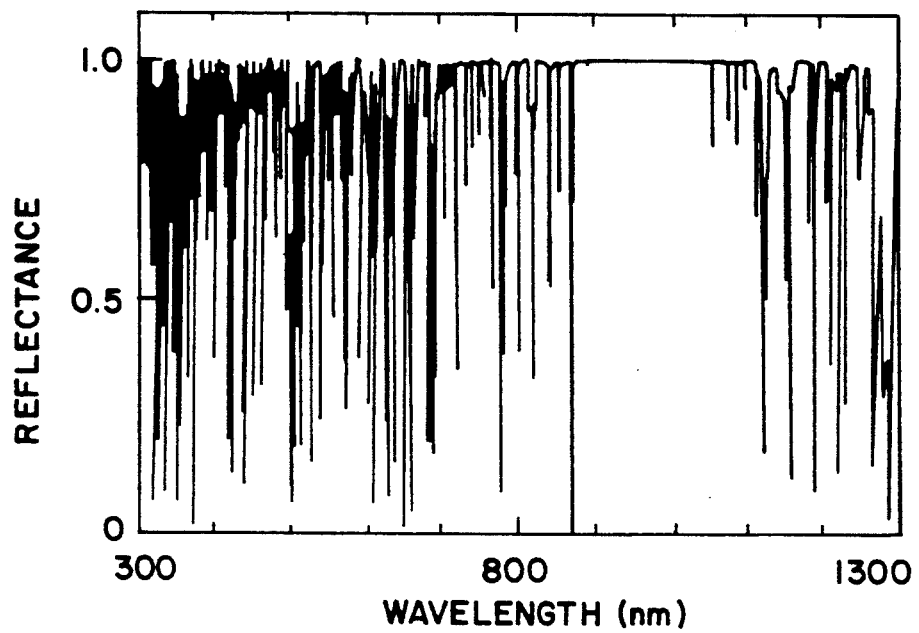
Figure 2D:
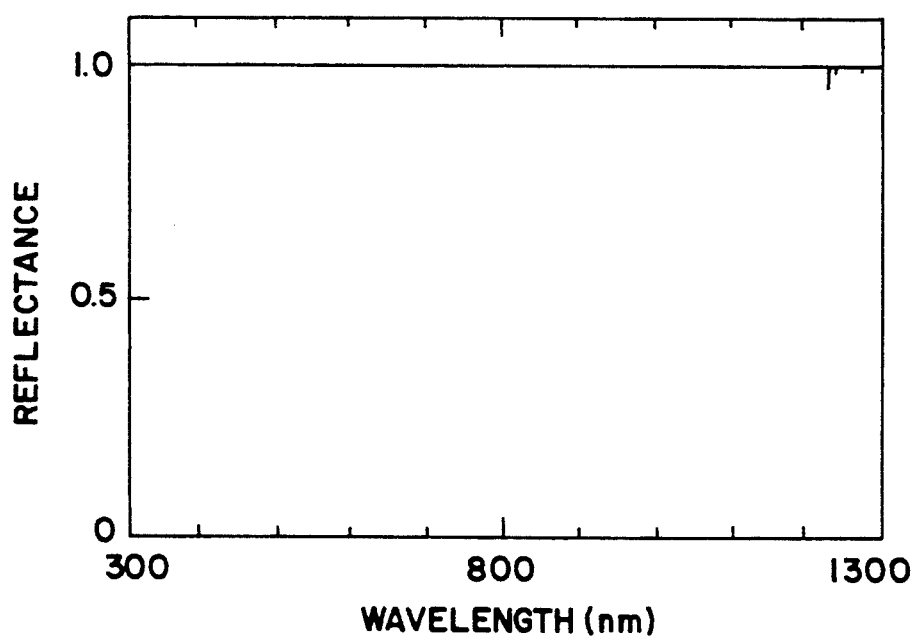

One of the most desirable characteristics of this nonlinear multilayer system is its active response to the intensity of the radiation, i.e., the higher the radiation intensity, the higher the rejection. This salient feature is illustrated in FIGS. 2(a) through 2(d), where the reflectance is shown to increase as the change in the refractive indices increases. The higher radiation intensity induces a larger refractive index, which results in higher interface reflectance $r_k$ and larger fluctuation of phase shift $d_k$. These changes increase the reflectance. FIGS. 2(a) through 2(d) show the respective cases of $n_{nl} = 0.01 n_1$, $0.08 n_1$, $0.2 n_1$, and $0.8 n_1$ for the high nonlinear refractive indices (the low non-linear refractive indices are assumed to be approximately zero). The number of layers is 400, the mean layer thickness is 380 nm, and the layer thickness is between 180 and 580 nm with white-noise fluctuation. The large fluctuation in reflectance shown in FIGS. 2(a) through 2(d) is a typical characteristic of an unordered system. The multilayer system is highly transmissive when the induced change in index is small, as seen in FIG. 2(a), where the change in index is 1% of $n_1$. The light will be totally reflected over a broad spectrum when the change in the refractive indices is sufficiently large. FIG. 2(d) shows such a total reflection from 300 to 1300 nm when $n_{n1}$ is $0.8n_1$.

Figure 3A:
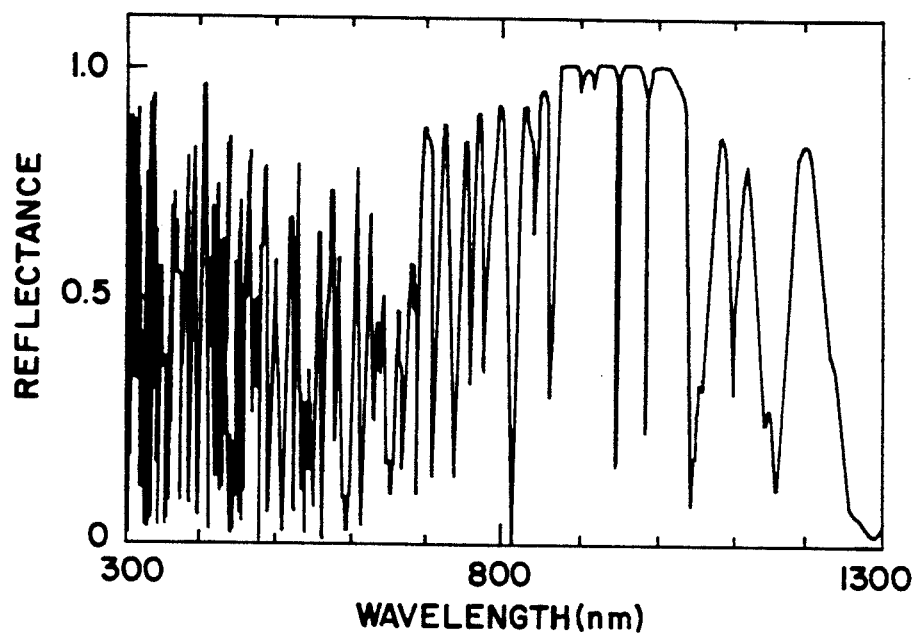
FIGS. 3(a) through 3(d) are computer-generated graphic representations of the reflectance of light as a function of wavelength for four different devices of the type shown in FIG. 1 wherein the linear index of refraction ($n_l$) for each layer in each device is 1.5, wherein the non-linear index of refraction ($n_{nl}$) for the high index materials is 0.2 $n_l$, wherein the number of layers in each device is 100, 400, 1000, and 2000, respectively, and wherein the optical thickness of each layer in each device is unordered, fluctuating between 180 nm and 580 nm with a mean thickness of about 380 nm.
Figure 3B:
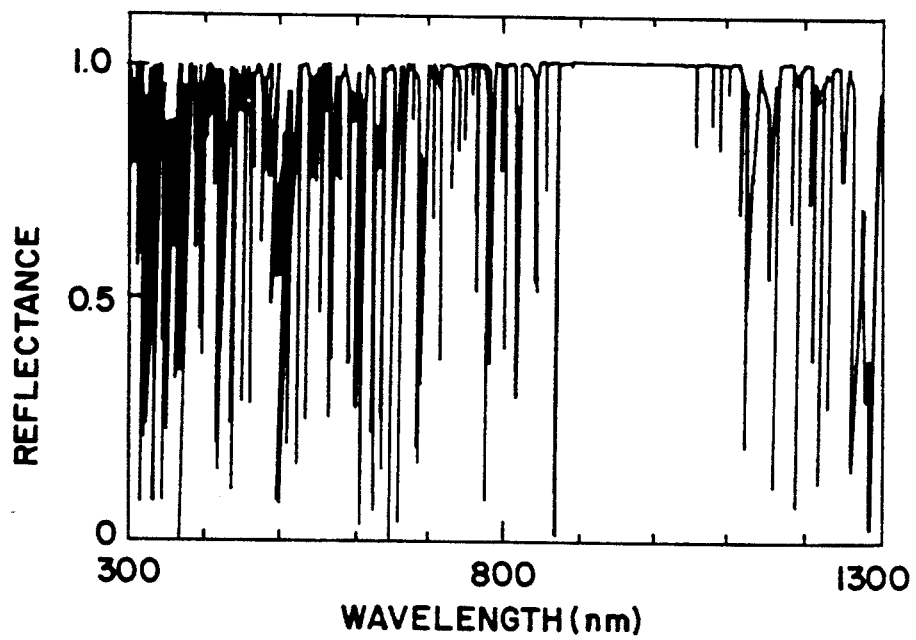
Figure 3C:
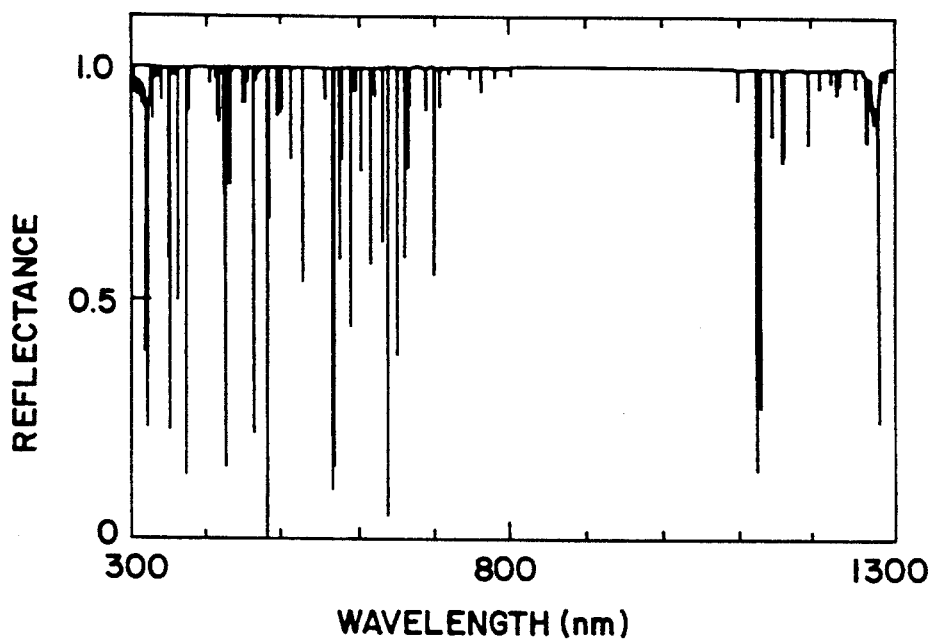
Figure 3D:
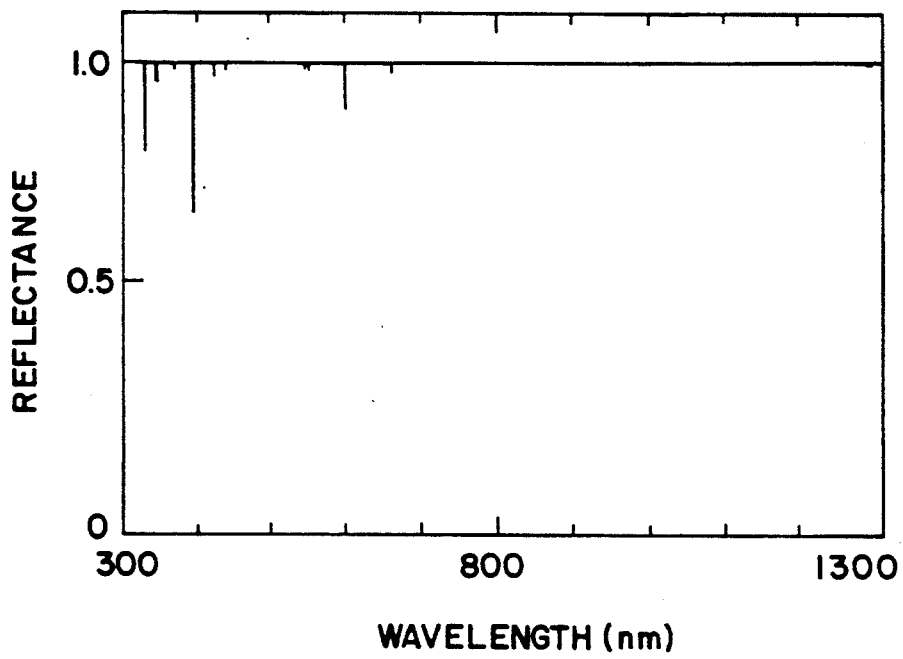

The rejection of light above some critical intensity level also depends on the number of layers in addition to the change in the refractive indices as illustrated above. If the change in the index is small, then a large number of layers will be required in order to reject the light of a given radiation intensity. FIGS. 3(a) through 3(d) show how the reflectance of the multilayer system increases as the number of layers increases, given a mean layer thickness of 380 nm and a thickness of between 180 and 580 nm. When the induced $n_{n1}$ is $0.2n_1$ for the high non-linear index layers (the low non-linear indices are assumed to be approximately zero), the light at many spectral regions is transmitted for a system with a small number of layers. FIG. 3(a) illustrates such an example for a 100-layer system. The bandwidth of the transmitted spectrum becomes narrower as the number of layers increases. When the number of layers is 2000, the system totally reflects the light over a broad bandwidth, as shown in FIG. 3(d).

The major advantage of the nonlinear mirror designed with an unordered layer thickness over that with a predetermined (ordered) layer thickness, as in the conventional broadband mirror, is that the random system will generate the broadest bandwidth of reflection. This extreme broadband reflection is necessary in order to protect one's eyes or a sensitive detector from all possible laser radiation spectra. In addition, a slight deviation of the layer thickness from the designated thickness of the random system will not affect the performance of reflection, which thus greatly simplifies the fabricating process. The performance of reflection for the unordered multilayer system is determined by the fluctuation (standard deviation) in layer thickness. If the system contains a sufficiently large number of layers such that the intense laser is totally reflected, then the laser incident at angles smaller than the Brewster angle will also be reflected at the spectral region near the center of the reflection band. This characteristic allows us to focus the laser beam into the multilayer system, which may be required in order to generate a high-intensity spot. Different angles of incidence of less than 30 degrees will change the mean and standard deviation of the phase shift by a factor of 2 or less. This amount of change will not have a significant effect on the total reflection near the center of the reflection band for a totally reflecting system.

The unordered system should reflect laser light of a broad spectrum, such as the pulsed laser. In photon localization, it is the coherent interference of the photon and its time-reversed counterpart that forbid the photon from propagating through the random layer. The coherent interference between two photons of different wavelengths should be negligible in an unordered system. Thus a broad-spectrum laser will be reflected in the unordered system.

Coating 13 of protective device 10 may be fabricated with currently available nonlinear materials. Two highly transmissive materials with linear refractive indices as close as possible are chosen here as an illustration. One such example of a high nonlinear index material is 2-methyl-4-nitroaniline (MNA). Its linear refractive index is 1.6, and its nonlinear coefficient $n_2$ is $6.56 \times 10^{-13}$ cm$^2$/W. This high nonlinear material may be used with a low nonlinear index material with a similar linear refractive index such as a glass (silicate EY-1). Another example of two materials which have the same linear index of refraction but different nonlinear indices of refraction and, therefore, may be used to make coating 13 is KDP and Silicate LSD glass. Other suitable materials for use in making coating 13 may be found in M. J. Weber, ed., *CRC Handbook of Laser Science and Technology*, (CRC Press, Boca Raton, Fla., 1986), page 274.

An unordered multilayer system of MNA/glass can protect one's eyes or a sensitive photodetector against radiation damage even for a low-power pulsed laser such as the colliding pulse mode-locked dye laser. The normal output parameters for the colliding-pulse mode-locked laser are 20 mW power, 82 MHz pulse repetition rate, 50-fs pulse, 5-mm beam diameter, and $\lambda = 620$ nm. This corresponds to an energy of 0.24 nJ/pulse or an average power of $5 \times 10^3$ W/pulse. In order for the laser pulse to be reflected from a 1500 layer system, the refractive index of MNA has to be increased by 0.32, or 20% of its linear index. This index change can be achieved by focusing the colliding-pulse mode-locked laser onto a $10^{-8}$ cm$^2$ spot by a 8 mm focal length lens. Higher power laser radiation can be rejected from the random system without a light focusing lens, while the lower power laser radiation may be rejected by choosing even higher nonlinear material. The system may reject the laser radiation over a wide range of laser powers if materials of high damage threshold are selected.

Figure 4:
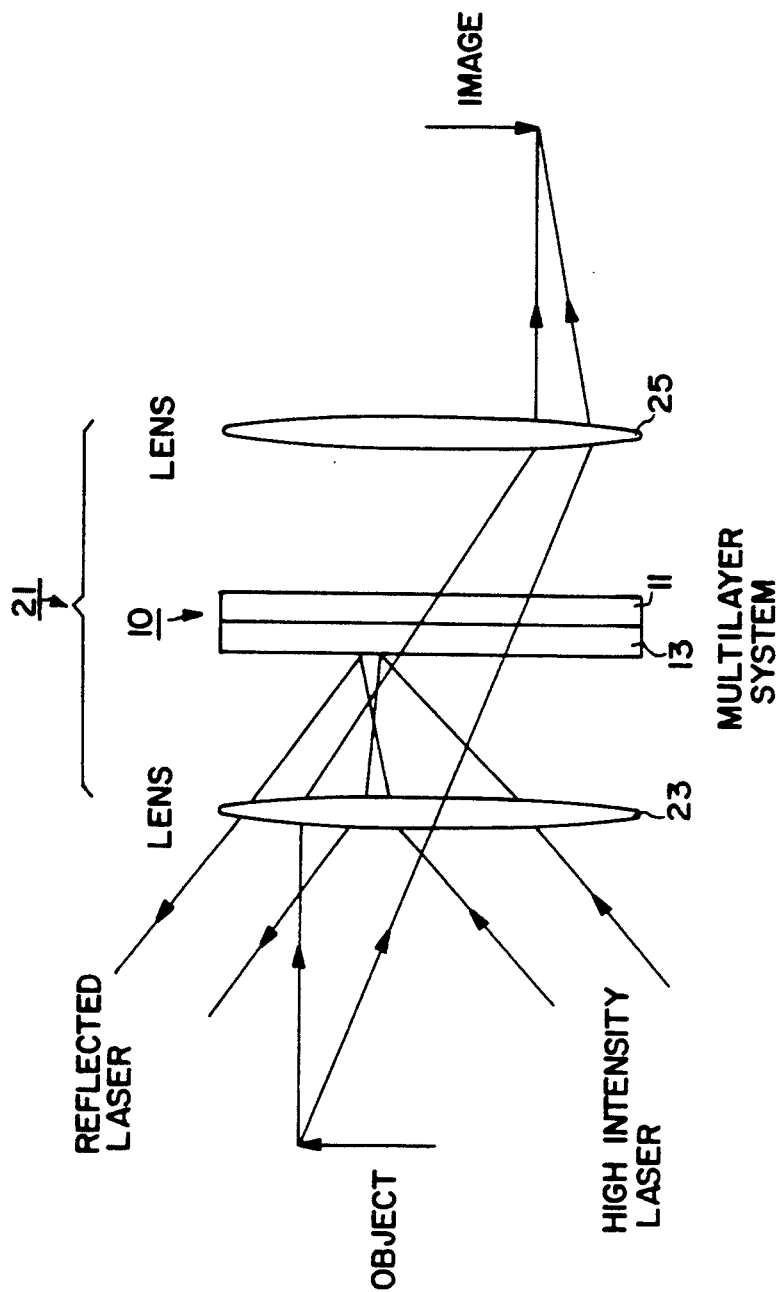
FIG. 4 is a schematic representation of an exemplary set-up which includes the protective device of FIG. 1 for use in reflecting high intensity light emitted from a laser source while transmitting low intensity light scattered from an object.

Referring now to FIG. 4, there is shown an exemplary set-up 21 which includes device 10. Set-up 21 may be particularly useful in a laser laboratory or the like where high intensity laser light is not uncommon. As can be seen, set-up 21 includes a first lens 23 which is used to focus both high-intensity light that has been emitted from a laser and low-intensity light that has been scattered from an object onto coating 13 of device 10. The principal reason for focusing the light onto coating 13 is to increase the intensity per unit area of the high-intensity light incident upon coating 13 so as to increase the degree of nonlinearity induced in coating 13 by the high-intensity light and, therefore, to maximize the reflectance thereof. A second lens 25 is placed on the opposite side of device 10 to focus the light transmitted by device 10 onto a suitable light detector.

As can be seen from FIG. 4, device 10 can simultaneously reflect high-intensity light while transmitting low-intensity and ambient light. It should be recognized, however, that if low-intensity and ambient light were to strike coating 13 at the same time and in the same location that high-intensity light were also striking coating 13, it too would be reflected by coating 13.

Figure 5:
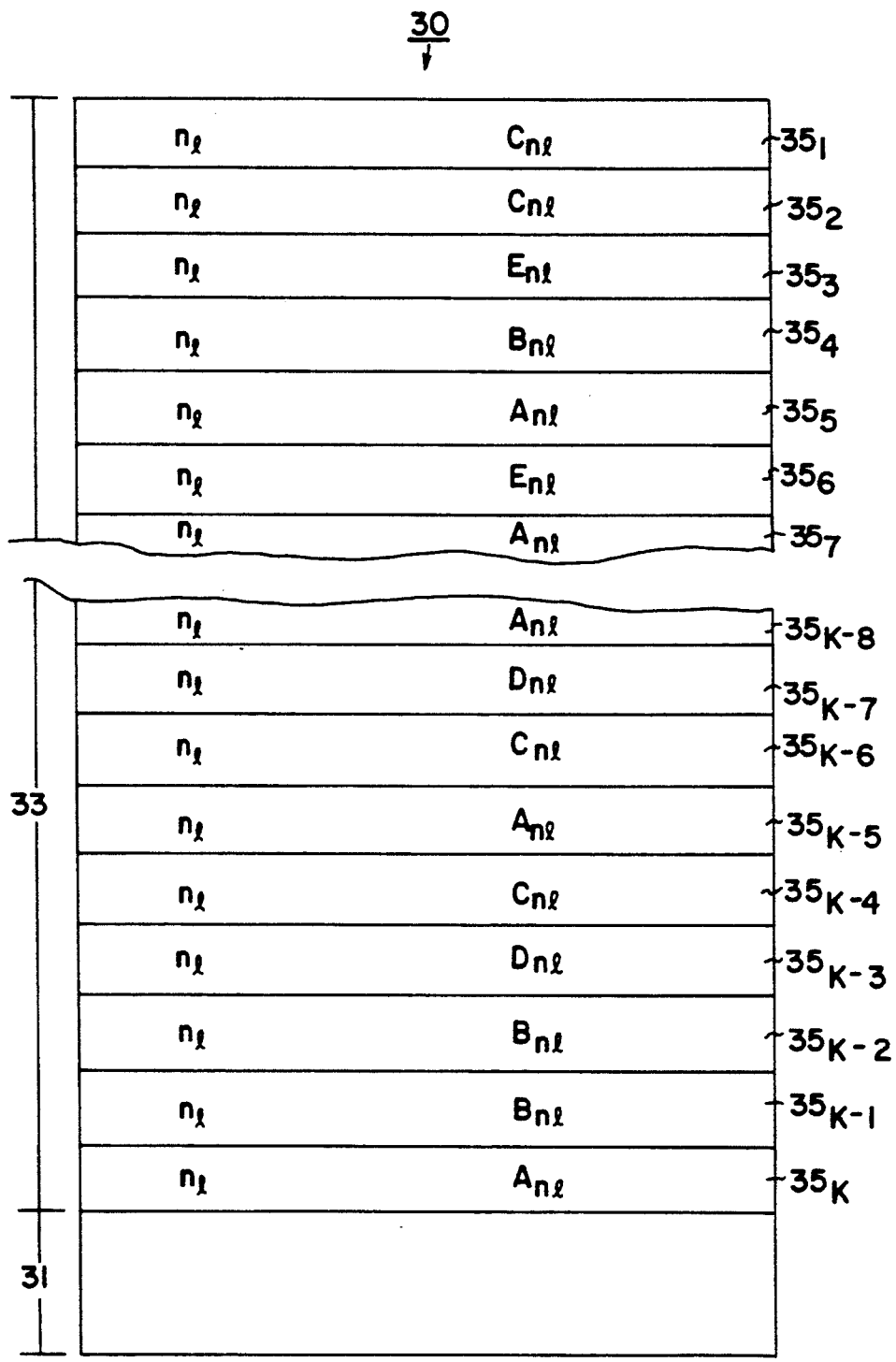
FIG. 5 is a schematic representation of a second embodiment of a protective device designed to selectively reflect an incident beam of high-intensity light over a broad spectral bandwith, the protective device being constructed according to the teachings of the present invention.

Referring now to FIG. 5, there is shown a second embodiment of a protective device designed to selectively reflect an incident beam of high-intensity light over a broad spectral bandwidth, the protective device being constructed according to the teachings of the present invention and being represented by reference numeral 30.

Device 30, like device 10, includes a transparent substrate 31 and a multilayer coating 33, coating 33 being affixed to substrate 31. Substrate 31 may be made of the same material that is used to make substrate 11 of device 10. Where, for example, device 30 is to be used as protective eyewear for a person, substrate 31 may be made of glass, plastic or the like.

Coating 33 comprises a stack of non-linear materials $35_1$ through $35_k$, respectively. All of the non-linear materials in the stack possess substantially the same linear index of refraction ($n_1$) and, in the embodiment shown, have substantially the same optical thickness of a one-half wavelength. As can readily be appreciated, these conditions permit low-intensity and ambient light to pass through the stack substantially unaffected. Each of the non-linear materials in the stack also possesses a non-linear index of refraction. The respective non-linear indices of refraction of the materials are not all the same, and materials $35_1$ through $35_k$ are arranged in the stack so that their respective non-linear indices of refraction are unordered. The unordered arrangement of materials $35_1$ through $35_k$ in the stack may be achieved with the aid of a computer as described above in connection with the fabrication of device 10.

As seen in FIG. 5, coating 30 comprises an unordered arrangement of a comparatively small class of different materials (i.e., a class of about 4–10 materials having the same linear index of refraction but different non-linear indices of refraction). An example of such a class is the class comprising the following materials: borosilicate BK7, cryolite, zirconium dioxide, magnesium fluoride, zinc sulfide, cerium fluoride, and titanium oxide.

It should be understood that, while coating 30 comprises only a relatively small number of different materials, coatings of this type should exhibit improved reflectance as the number of different materials having the same linear index of refraction but different nonlinear indices of refraction increases, as the variation in the respective nonlinear indices of refraction increases, or as the number of layers in the coating increases.

Figure 6:
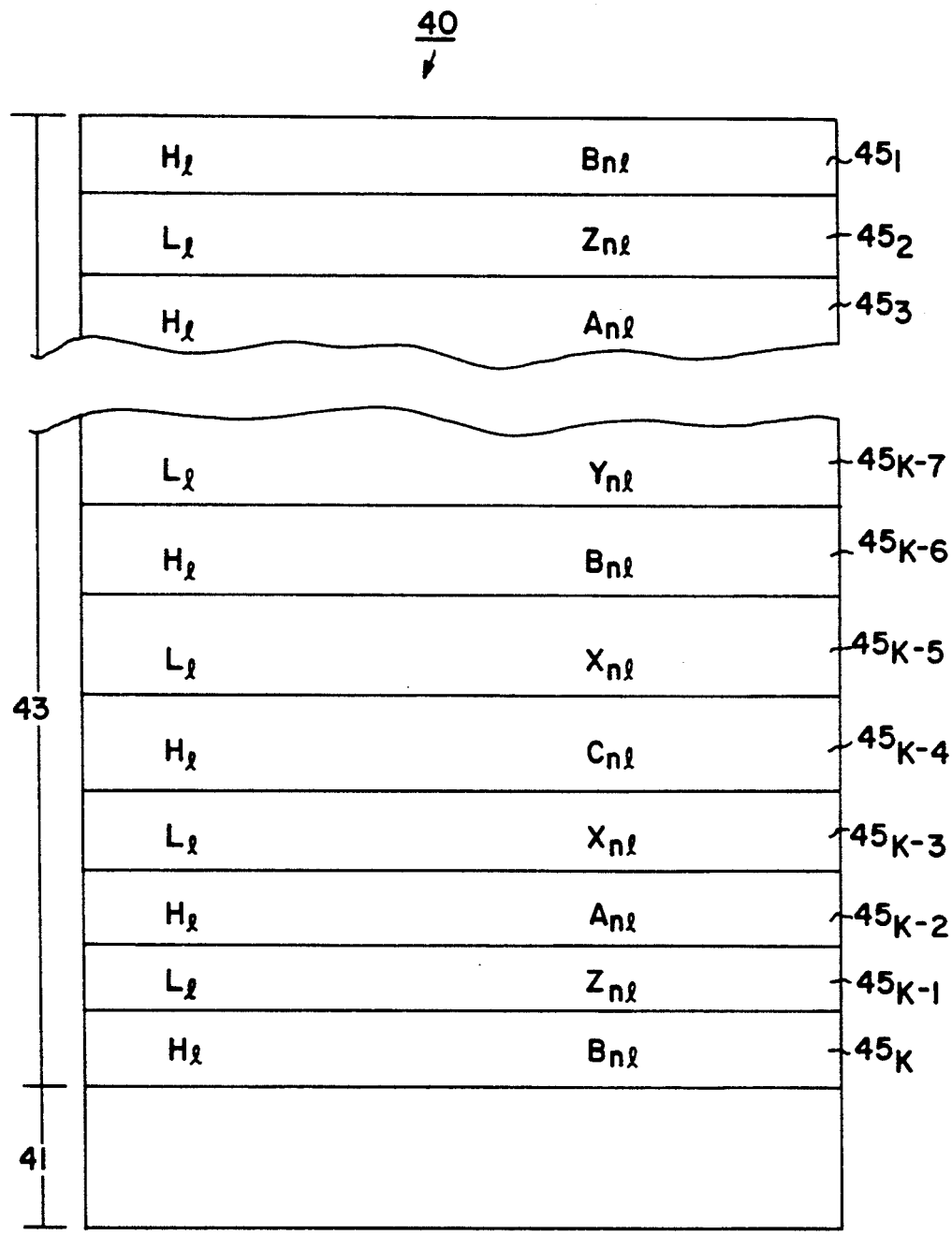
FIG. 6 is a schematic representation of a third embodiment of a protective device designed to selectively reflect an incident beam of high-intensity light over a broad spectral bandwith, the protective device being constructed according to the teachings of the present invention.

Referring now to FIG. 6, there is shown a third embodiment of a protective device designed to selectively reflect an incident beam of high-intensity light over a broad spectral bandwidth, the protective device being constructed according to the teachings of the present invention and being represented by reference numeral 40.

Device 40, like devices 10 and 30, includes a transparent substrate 41 and a multilayer coating 43, coating 43 being affixed to substrate 41. Substrate 41 may be made of the same material that is used to make substrate 11 of device 10. Where, for example, device 40 is to be used as protective eyewear for a person, substrate 41 may be made of glass, plastic or the like.

Coating 43 comprises a stack of non-linear materials $45_1$ through $45_k$, respectively. Materials $45_1$ through $45_k$ are arranged in the stack so that their linear indices of refraction alternate between a relatively high linear index of refraction and a relatively low linear index of refraction whereas the non-linear indices of refraction are unordered. The optical thicknesses of the respective materials are designed to optimize the transmissivity of the stack in the linear domain.

To arrange the nonlinear materials in the stack according to the criteria described above, one may use a computer in substantially the same manner as described above in connection with the fabrication of coating 33 of device 30, the principal difference being that two classes of materials (one class consisting of low linear index materials having different nonlinear indices, the other class consisting of high linear index materials having different nonlinear indices) must be used to make coating 43 whereas only one class of materials (a class consisting of materials having the same linear index and different nonlinear indices) was needed to make coating 33.

Figure 7:
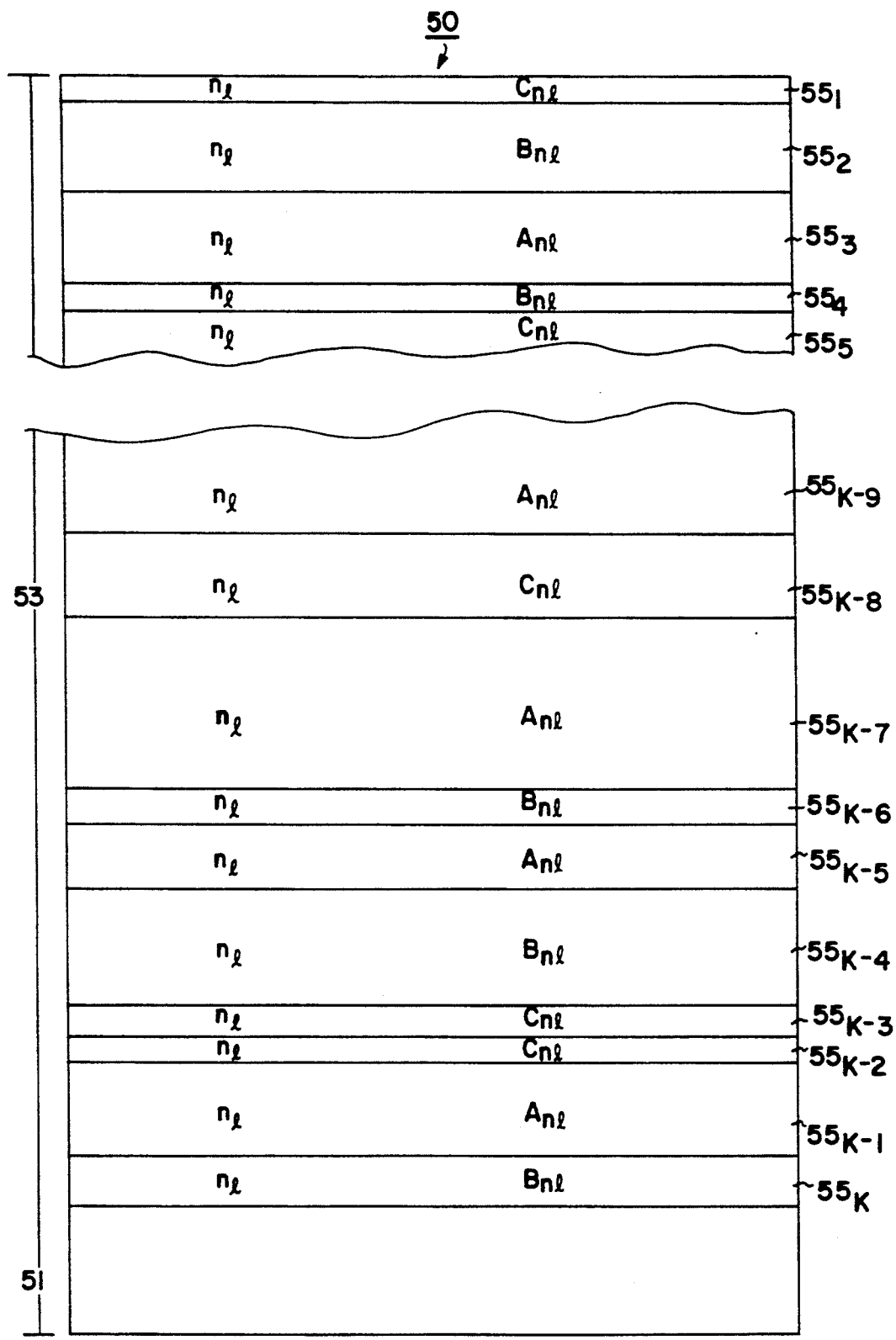
FIG. 7 is a schematic representation of a fourth embodiment of a protective device designed to selectively reflect an incident beam of high-intensity light over a broad spectral bandwith, the protective device being constructed according to the teachings of the present invention.

Referring now to FIG. 7, there can be seen a fourth embodiment of a device constructed according to the teachings of the present invention, the device being represented generally by reference numeral 50.

Device 50 comprises a transparent substrate 51 and a multilayer coating 53, coating 53 being affixed to substrate 51. Substrate 51 may be made of the same material as substrate 31 of device 30. Coating 53, which comprises a plurality of nonlinear materials $55_1$ through $55_k$, is similar in construction and composition to coating 33 of device 30, the principal difference between the two coatings being that the optical thicknesses of the nonlinear materials 55 of device 50 are unordered instead of each being a one-half wavelength.

The embodiments of the present invention described above are intended to be merely exemplary and those skilled in the art shall be able to make numerous variations and modifications to it without departing from the spirit of the present invention. All such variations and modifications are intended to be within the scope of the present invention as defined by the appended claims.

What is claimed is:

1. A protective device designed to selectively reflect an incident beam of high-intensity light over a broad spectral bandwidth, the protective device comprising a stack of nonlinear materials, each of said nonlinear materials possessing a linear index of refraction, a nonlinear index of refraction, and an optical thickness, the respective linear indices of refraction of said nonlinear materials being the same, the respective nonlinear indices of refraction of said nonlinear materials alternating between a relatively high nonlinear index of refraction and a relatively low nonlinear index of refraction, and the respective optical thicknesses of said nonlinear materials being unordered.

2. The protective device as claimed in claim 1 wherein the respective optical thicknesses of said nonlinear materials are selected with the use of a random number generator.

3. The protective device as claimed in claim 1 wherein said stack comprises 400 layers of nonlinear materials, wherein the linear index of refraction for all of said nonlinear materials is 1.5, wherein the nonlinear index of refraction for said nonlinear materials possessing a relatively high nonlinear index of refraction is at least 0.015, wherein the nonlinear index of refraction for said nonlinear materials possessing a relatively low nonlinear index of refraction is approximately zero, and wherein the optical thickness of each of said nonlinear materials is between 180 nm and 580 nm.

4. The protective device as claimed in claim 3 wherein the nonlinear index of refraction for said nonlinear materials possessing a relatively high nonlinear index of refraction is at least 0.12.

5. The protective device as claimed in claim 4 wherein the nonlinear index of refraction for said nonlinear materials possessing a relatively high nonlinear index of refraction is at least 0.3.

6. The protective device as claimed in claim 5 wherein the nonlinear index of refraction for said nonlinear materials possessing a relatively high nonlinear index of refraction is at least 1.2.

7. The protective device as claimed in claim 1 wherein said stack comprises at least 100 layers, wherein the linear index of refraction for all of said nonlinear materials is 1.5, wherein the nonlinear index of refraction for said nonlinear materials possessing a relatively high nonlinear index of refraction is 0.3, wherein the nonlinear index of refraction for said nonlinear materials possessing a relatively low nonlinear index of refraction is approximately zero, and wherein the optical thickness of each of said nonlinear materials is between 180 nm and 580 nm.

8. The protective device as claimed in claim 7 wherein said stack comprises at least 400 layers.

9. The protective device as claimed in claim 8 wherein said stack comprises at least 1000 layers.

10. The protective device as claimed in claim 9 wherein said stack comprises at least 2000 layers.

11. The protective device as claimed in claim 1 wherein said nonlinear material possessing a relatively high nonlinear index of refraction is 2-methyl-4-nitroaniline and wherein said nonlinear material possessing a relatively low nonlinear index of refraction is silicate EY-1.

12. A protective device designed to selectively reflect high-intensity light over a broad spectral bandwidth, the protective device comprising a stack of non-linear materials, each of said nonlinear materials in said stack possessing a linear index of refraction and a nonlinear index of refraction, the respective linear indices of refraction of said nonlinear materials being the same, the respective nonlinear indices of refraction of said nonlinear materials being unordered.

13. The protective device as claimed in claim 12 wherein said nonlinear materials include at least two materials selected from the group consisting of borosilicate BK7, cryolite, zirconium dioxide, magnesium fluoride, zinc sulfide, cerium fluoride, and titanium oxide.

14. The protective device as claimed in claim 12 wherein said nonlinear indices of refraction are selected with the use of a random number generator.

15. The protective device as claimed in claim 12 wherein each of said nonlinear materials in said stack also possesses an optical thickness, the respective optical thicknesses of said nonlinear materials being unordered.

16. A protective device designed to selectively reflect high-intensity light over a broad spectral bandwidth, the protective device comprising a stack of nonlinear materials, each of said nonlinear materials in said stack possessing a linear index of refraction, a nonlinear index of refraction, and an optical thickness, the respective linear indices of refraction of the non-linear materials alternating between a high index of refraction and a low index of refraction, the respective optical thicknesses of the nonlinear materials being such that said stack of nonlinear materials is highly transmissive in the linear domain, the respective nonlinear indices of refraction of said nonlinear materials being unordered.

17. The protective device as claimed in claim 16 wherein said nonlinear indices of refraction are selected with the use of a random number generator.

* * * * *